US00PP22190P2

(12) United States Plant Patent
Warner

(10) Patent No.: US PP22,190 P2
(45) Date of Patent: Oct. 11, 2011

(54) ROSE PLANT NAMED 'CHEWPERADVENTURE'

(50) Latin Name: *Rosa hybrida*
Varietal Denomination: Chewperadventure

(75) Inventor: Christopher Hugh Warner, Newport (GB)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,832

(22) Filed: Sep. 14, 2010

(51) Int. Cl.
*A01H 5/00* (2006.01)

(52) U.S. Cl. ..... Plt./108

(58) Field of Classification Search ..... Plt./108, Plt./106, 107
See application file for complete search history.

*Primary Examiner* — Kent L Bell
(74) *Attorney, Agent, or Firm* — C. A. Whealy

(57) ABSTRACT

A new and distinct cultivar of Rose plant named 'Chewperadventure', characterized by its outwardly spreading and low mounding plant habit; glossy dark green-colored leaflets; freely branching growth habit; dense and bushy plant form; freely and continuous flowering habit; large salmon red-colored flowers; resistance to Black Spot; and good garden performance.

2 Drawing Sheets

Botanical designation: *Rosa hybrida.*
Cultivar denomination: 'CHEWPERADVENTURE'.

BACKGROUND OF THE INVENTION

The present Invention relates to a new and distinct cultivar of Rose plant, botanically known as *Rosa hybrida*, commercially used as an ornamental shrub and hereinafter referred to by the name 'Chewperadventure'.

The new Rose plant is a product of a planned breeding program conducted by the Inventor in Brockton, Newport, Shophire, United Kingdom. The objective of the breeding program was to develop new ground cover Rose plants with improved disease resistance and attractive flower coloration.

The new Rose plant originated from a cross-pollination made by the Inventor in 1997 of *Rosa hybrida* 'Chewpobey', not patented, as the female, or seed, parent with an unnamed selection of *Rosa hybrida*, not patented, as the male, or pollen, parent. The new Rose plant was discovered and selected by the Inventor as a single flowering plant within the progeny of the stated cross-pollination in a controlled environment in Brockton, Newport, Shophire, United Kingdom.

Asexual reproduction of the new Rose plant by softwood cuttings at Brockton, Newport, Shophire, United Kingdom since 2000, has shown that the unique features of this new Rose plant are stable and reproduced true to type in successive generations of asexual reproduction.

SUMMARY OF THE INVENTION

The following traits have been repeatedly observed and are determined to be the unique characteristics of 'Chewperadventure'. These characteristics in combination distinguish 'Chewperadventure' as a new and distinct Rose plant:

1. Outwardly spreading and low mounding plant habit.
2. Glossy dark green-colored leaflets.
3. Freely branching growth habit, dense and bushy plant form.
4. Freely and continuous flowering habit.
5. Large salmon red-colored flowers.
6. Resistant to Black Spot.

7. Good garden performance.

Plants of the new Rose differ from plants of the female parent, 'Chewpobey', in the following characteristics:

1. Plants of the new Rose have larger leaves and leaflets than plants of 'Chewpobey'.
2. Plants of the new Rose have larger flowers than plants of 'Chewpobey'.
3. Plants of the new Rose and 'Chewpobey' differ in flower color as plants of 'Chewpobey' have orange red-colored flowers.

Plants of the new Rose differ from plants of the male parent selection in the following characteristics:

1. Plants of the new Rose are more low mounding than and not as upright as plants of the male parent selection.
2. Plants of the new Rose and the male parent selection differ in flower color as plants of the male parent selection have pink-colored flowers.

Plants of the new Rose can be compared to plants of *Rosa hybrida* 'Horcoherent', disclosed in U.S. Plant Pat. No. 15,982. In side-by-side comparisons, plants of the new Rose differ primarily from plants of 'Horcoherent' in the following characteristics:

1. Plants of the new Rose flower more continuously during the flowering season than plants of 'Horcoherent'.
2. Plants of the new Rose and 'Horcoherent' differ in flower color as plants of 'Horcoherent' have orange, pink and yellow-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type.

Colors in the photographs may differ slightly from the color values cited in the detailed botanical description which accurately describe the colors of the new Rose plant.

The photograph on the first sheet comprises a side perspective view of a typical plant of 'Chewperadventure' ground in an outdoor nursery.

The photograph on the second sheet is a close-up view of a typical flowering plant of 'Chewperadventure'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown during the summer in Grand Haven, Mich., in an outdoor nursery and under commercial Rose production practices. Plants were about three years old when the photographs and description were taken. In the following description, color references are made to The Royal Horticultural Society Colour Chart, 2001 Edition, except where general terms of ordinary dictionary significance are used.

Botanical classification: *Rosa hybrida* 'Chewperadventure'

Parentage:

*Female, or seed, parent.*—*Rosa hybrida* 'Chewpobey', not patented.

*Male, or pollen, parent.*—Unnamed selection of *Rosa hybrida*, not patented.

Propagation:

*Type.*—By softwood cuttings.

*Time to initiate roots, summer.*—About 15 days at 24° C.

*Time to produce a rooted young plant, summer.*—About three months at 24° C.

*Root description.*—Fibrous; white in color.

*Rooting habit.*—Freely branching; dense.

Plant description:

*Plant form.*—Outwardly spreading and low mounding perennial shrub.

*Growth habit.*—Moderately vigorous growth habit; freely branching habit; about 52 lateral branches developing per plant; dense and bushy plant form.

*Plant height.*—About 60 cm.

*Plant width (spread).*—About 1 meter.

*Lateral branches.*—Length: About 33 cm. Diameter: About 3 mm. Internode length: About 2.2 cm. Strength: Strong. Texture: Smooth, glabrous. Color: Close to 144A tinged with close to 46A. Thorns: Density: About one to two per internode. Shape: Triangular with sharp acuminate apices. Height: About 3 mm. Diameter, at base: About 2 mm. Color: Close to 144A overlain with 59A.

Foliage description:

*Arrangement.*—Alternate; compound with about five to seven leaflets.

*Leaflet length.*—About 2.2 cm.

*Leaflet width.*—About 1.4 cm.

*Leaflet shape.*—Ovate.

*Leaflet apex.*—Acute.

*Leaflet base.*—Obtuse.

*Leaflet margin.*—Serrulate.

*Leaflet texture, upper and lower surfaces.*—Smooth, glabrous.

*Leaflet luster, upper and lower surfaces.*—Glossy.

*Leaflet venation pattern.*—Pinnate.

*Leaflet color.*—Developing leaflets, upper surface: Close to 137A tinged with close to 46B. Developing leaflets, lower surface: Close to 146A tinged with close to 46B. Fully expanded leaflets, upper surface: Close to 146A to 146B; venation, close to 146A. Fully expanded leaflets, lower surface: Close to 146D; venation, close to 146D.

*Leaf petiole.*—Length: About 1.5 cm. Diameter: About 1 mm. Texture, upper and lower surfaces: Smooth, glabrous. Color, upper and lower surfaces: Close to 144B.

Flower description:

*Flower type and habit.*—Double rotate flowers arranged in terminal clusters with about five flowers per cluster; flowers face mostly upright or outwardly.

*Natural flowering season.*—Plants flower in the garden from June until frost in Grand Haven, Mich., during this period flowering is continuous; plants begin flowering about six weeks after planting.

*Postproduction longevity.*—Flowers typically last about seven to twelve days on the plant and about ten days as a cut flower; flowers not persistent.

*Fragrance.*—Slightly fragrant; sweet, pleasant.

*Flower buds.*—Height: About 1 cm. Diameter: About 6 mm. Shape: Ovoid. Color: Close to 144A to 144B.

*Flowers.*—Diameter: About 5 cm to 6 cm. Depth: About 5 cm.

*Petals.*—Quantity per flower: About 20 in three to four whorls. Length: About 2.2 cm. Width: About 2 cm. Shape: Broadly obovate. Apex: Obtuse or slightly mucronate. Base: Attenuate. Margin: Entire. Texture, upper and lower surfaces: Smooth, glabrous. Color: Developing, upper surface: Close to 52A. Developing, lower surface: Close to 52C. Fully expanded, upper surface: Close to 41A; color becoming closer to 52C with development. Fully expanded, lower surface: Close to 52C.

*Sepals.*—Quantity per flower: Five. Length: About 1.5 cm. Width: About 5 mm. Shape: Lanceolate. Apex: Acuminate. Base: Fused. Margin: Entire. Texture, upper and lower surfaces: Slightly pubescent. Color: Developing and fully expanded, upper surface: Close to 138B. Developing and fully expanded, lower surface: Close to 138A.

*Peduncles.*—Length: About 3 cm. Diameter: About 1.5 mm. Orientation: Erect to about 20° from vertical. Strength: Strong. Color: Close to 144B.

*Reproductive organs.*—Stamens: Quantity per flower: Numerous, about 120. Anther shape: Oblong. Anther size: About 0.5 mm by 1 mm. Anther color: Close to 17A. Pollen amount: Moderate. Pollen color: Close to 17A. Pistils: Quantity per flower: About 20. Pistil length: About 3 mm. Stigma shape: Rounded. Stigma color: Close to 34A. Style length: About 2.9 mm. Style color: Close to 34A. Ovary color: Close to 144B. Seeds: Length: About 2 mm. Diameter: About 1 mm. Color: Close to 200A.

Pathogen/pest resistance: Plants of the new Rose have been observed to be resistant to Black Spot. Plants of the new Rose have not been observed to be resistant to pests and other pathogens common to Roses.

Garden performance: Plants of the new Rose have been observed have good garden performance and to tolerate rain, wind and temperatures ranging from about −26° C. to about 36° C.

It is claimed:

1. A new and distinct Rose plant named 'Chewperadventure' as illustrated and described.

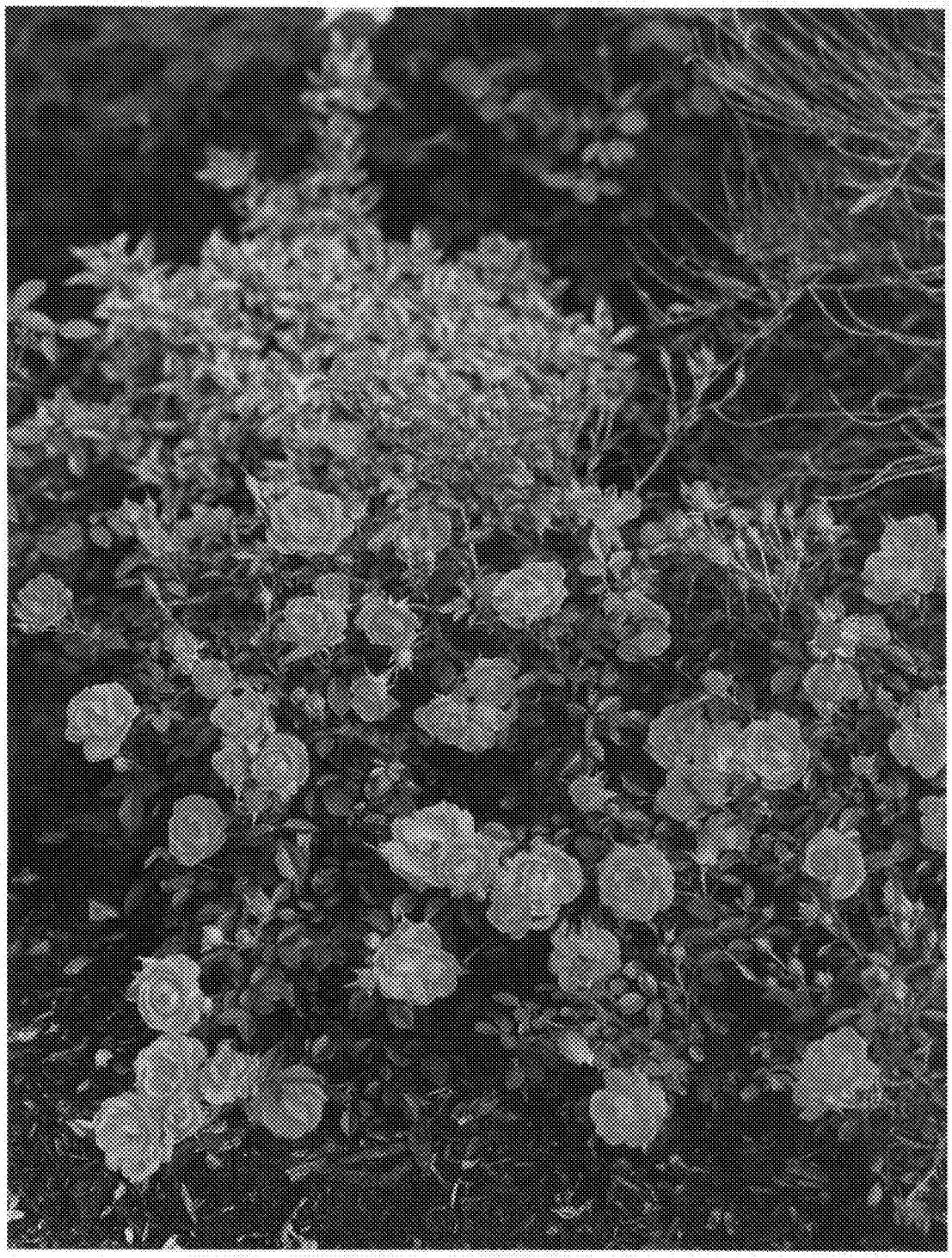

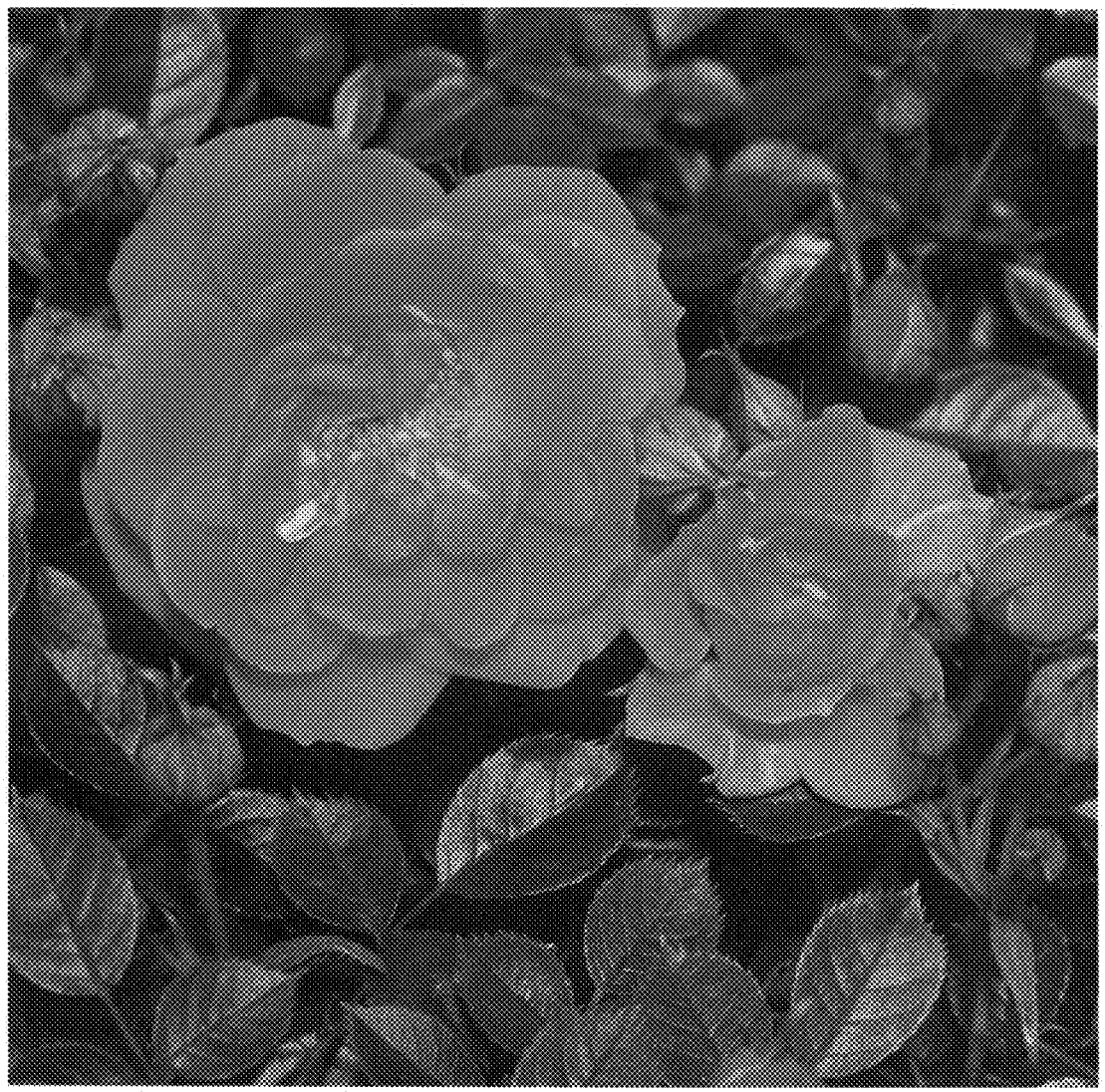

* * * * *